United States Patent [19]

Mori

[11] Patent Number: 4,802,066
[45] Date of Patent: Jan. 31, 1989

[54] BED EMPLOYED FOR LIGHT BATHING

[76] Inventor: Kei Mori, 3-16-3-501, Kaminoge, Setagayu-ku, Tokyo, Japan

[21] Appl. No.: 58,090

[22] Filed: Jun. 4, 1987

[30] Foreign Application Priority Data

Jun. 10, 1986 [JP] Japan ............... 61-134306

[51] Int. Cl.$^4$ .............. F21V 7/04; A47B 23/06
[52] U.S. Cl. ........................ 362/32; 362/31; 362/127; 362/130; 5/508; 5/2 R
[58] Field of Search ............ 362/31, 32, 127, 130; 5/508, 2 R

[56] References Cited

U.S. PATENT DOCUMENTS

| | | | |
|---|---|---|---|
| 1,526,132 | 2/1925 | Gilgar | 362/131 |
| 2,825,337 | 3/1958 | Illfender | 362/131 |
| 3,892,959 | 7/1975 | Pulles | 362/31 |
| 4,096,550 | 6/1978 | Bollar et al. | 362/31 |
| 4,151,582 | 4/1979 | Grunbarger | 362/31 |
| 4,220,984 | 9/1980 | Truher et al. | 362/130 |
| 4,233,649 | 11/1980 | Scheer et al. | 362/131 |
| 4,234,907 | 11/1980 | Daniel | 362/32 |
| 4,277,817 | 7/1981 | Hebr | 362/31 |
| 4,286,839 | 9/1981 | Ibzig et al. | 362/32 |
| 4,422,719 | 12/1983 | Orcult | 362/32 |
| 4,677,531 | 6/1987 | Szeles | 362/32 |

Primary Examiner—Raymond Nelli
Attorney, Agent, or Firm—Jordan and Hamburg

[57] ABSTRACT

A bed employed for use in light bathing. The bed comprises a transparent cloth stretched thereon and optical conductors arranged on the underside of the cloth. The optical conductors are arranged in such a manner that the light rays transmitted therethrough are radiated outside of the optical conductors and pass through the transparent cloth.

2 Claims, 2 Drawing Sheets

BED EMPLOYED FOR LIGHT BATHING

BACKGROUND OF THE INVENTION

The present invention relates to a bed employed for use in light bathing.

The present applicant has previously proposed to focus solar rays or artificial light rays by the use of lenses or the like, to guide the same into an optical conductor, and to transmit those solar rays or artificial light rays onto an optional desired place through the optical conductor. Those light rays transmitted in such a way are employed for use in illuminating or for other like purposes, as for example to cultivate plants, chlorella or the like. In the process thereof, visible light rays not containing ultraviolet rays, infrared rays, etc., are used to promote a living body reaction, and thereby to promote the health of a person.

On the basis of such a discovery, the present applicant has previously proposed various light ray radiating devices for health and beauty treatment and capable of radiating light rays that correspond to the visible light ray components of solar rays and which do not contain therein any harmful components such as ultraviolet rays, infrared rays, etc. An example thereof is U.S. Pat. No. 4,653,472 issued Mar. 30, 1987, which is incorporated herein by reference. Such beneficial light rays are focused onto specific parts of a patient in order to radiate the same to give beauty treatments and to promote health, etc.

It is well known that sun-bathing is useful for promoting the human body's health. However, ultraviolet or the like are contained in the solar rays and exert a bad influence on the skin of the human body. The person who is not so healthy to begin with cannot bathe in the sun.

Furthermore, light rays such as ultraviolet, infrared or the like have an accumulation effect. Accumulating ultraviolet causes cancer, and accumulating infrared causes a heat or is even capable of producing a burn. Consequently, it is worse for the health to bathe in light rays containing therein ultraviolet or infrared for a long time.

As mentioned above, light rays radiated onto the specific parts of the patient are to be the light rays corresponding to the visible light rays component of solar rays containing therein neither ultraviolet nor infrared. Thereby, health and beauty treatment can be done without resulting in any adverse influence due to ultraviolet and infrared.

SUMMARY OF THE INVENTION

It is an object of the present invention to provide a bed for bathing in light, the light rays consisting of only a visible light rays component and not containing therein any harmful component such as ultraviolet, infrared or the like.

It is another object of the present invention to provide a bed for bathing in light, the visible light rays being radiated from optical conductors which are embedded in the bed.

It is another object of the present invention to provide a bed employed for light bathing which can be preferably used by an aged person who is confined to a bed.

The above-mentioned features and other advantages of the present invention will be apparent from the following detailed description taken in conjunction with the accompanying drawings.

DETAILED DESCRIPTION OF THE PREFERRED EMBODIMENTS

Figure 1:
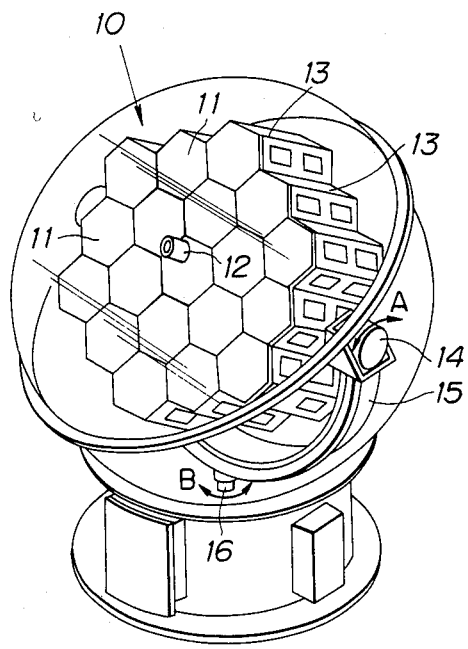
FIG. 1 is a structural view illustrating an embodiment of a solar ray collecting device which is employed for bringing the present invention into operation.

FIG. 1 is a detailed structural view of a solar ray collecting device 10 which is accommodated in a transparent dome-shaped capsule. The solar ray collecting device 10 comprises a large number of lenses 11 (nineteen lenses in the embodiment shown in FIG. 1), a solar rays direction sensor 12 for detecting the direction of the solar rays, a support frame 13 for unitarily sustaining the lenses 11 and the solar rays direction sensor 12, a first motor 14 for rotatably moving in a direction shown by an arrow A the unitarily combined lenses 11, sensor 12, and support frame 13, a support arm 15 for supporting the afore-mentioned lenses 11, sensor 12, support frame 13, and motor 14, a rotatable shaft 16 installed so as to meet at a right angle with the rotatable shaft of the afore-mentioned motor 14, and a second motor not shown in FIG. 1 for rotating the rotatable shaft 16 in a direction shown by an arrow B.

The direction of the solar rays is detected by the afore-mentioned solar rays direction sensor 12. The signal generated by the sensor 12 controls the first motor and the second motor so as to direct the lenses 11 toward the sun at all times. The solar rays focused by the lenses 11 are guided into the optical conductor cable, the light receiving end portion of which is located at the focus position of the lenses 11, and further, the solar rays are transmitted through the optical conductor cable to a specific part of the patient.

Figure 2:
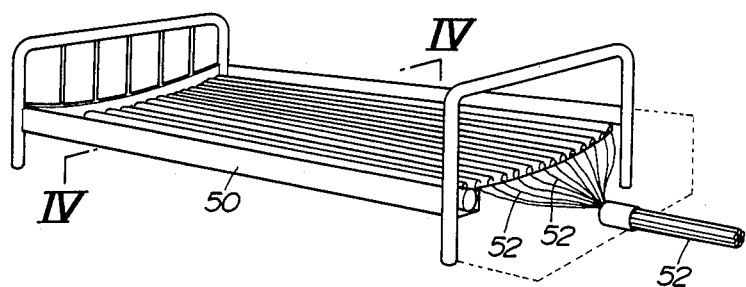
FIG. 2 is a construction view illustrating the main body of an embodiment of a bed to be used for light bathing according to the present invention.
Figure 3:
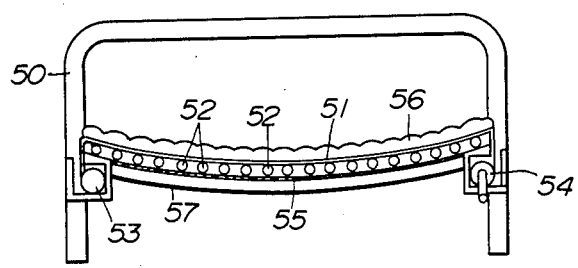
FIG. 3 is a view taken along section line III—III of FIG. 2.

FIG. 2 is an overall perspective view of the main body of an embodiment of a bed employed for light bathing according to the present invention. FIG. 3 is a view of its construction as seen along the line III—III of FIG. 2. In FIGS. 2 and 3, there is shown the frame 50 of the bed, a transparent cloth 51, and optical conductors 52. In the present invention, the transparent cloth 51 is stretched onto the frame 50 of the bed and a large number of optical conductors 52 are arranged on the underside of it. The light rays emitted from the optical conductors 52 pass through the cloth 51. The light rays are then radiated onto a human body lying on the cloth 51.

A solar ray collecting device or an artificial light ray collecting device, proposed previously by the present applicant, is installed at the end portion of the optical conductor 52 (not shown). The light rays focused by the solar ray collecting device or the artificial light rays are guided into the optical conductor 52. The guided light rays are transmitted through the optical conductor 52 and emitted outside of it at the lowerside of the transparent cloth 51 arranged on the bed 50 as mentioned before.

One who employs the bed can receive a light bath by lying naked on the stretched cloth as mentioned above. Any transparent material can be used as the above-mentioned cloth. If possible, it is preferable to use a material that is gentle to human skin, as, for example, silk.

Furthermore, since the user lies on the cloth naked and since silk cloth is weak, it may be preferable that the cloth be stretched in such a way as to be interchangeable with others for private use as well as for common use. It is simple to prepare a plurality of cloths and to use those cloths one after another.

However, in order to avoid exchanging, cleaning and disinfecting the cloth, the cloth is wound into a rolled state as shown in FIG. 3. A roller 53 having the cloth wound thereon is installed at one side of the bed 50 and a roller 54 for unwinding it is installed at the other side of the bed 50. In such a way, it may be possible to stretch a new part of the cloth 51 by turning the windout roller 54 when the cloth 51 becomes dirty or wears out.

Furthermore, in the case of only stretching the cloth onto the bed, the cloth might get torn when a person uses on the bed. For this reason, a reinforcing material 55 such as steel wire netting, netted sheeting, or transparent cloth is placed under the cloth 51 or the optical conductor 52. Furthermore, an air bag 56 constructed of a transparent material is placed on the cloth 51. In such a manner, the bed becomes very comfortable to lie on and to sleep in.

Figure 4:
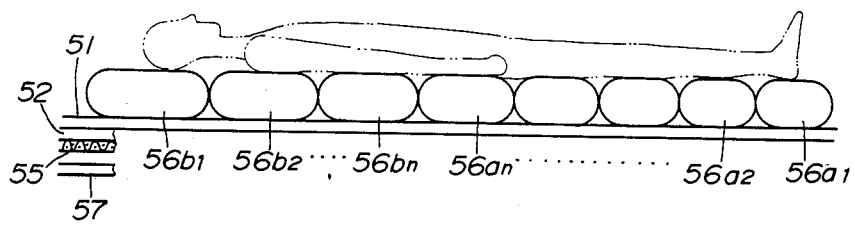
FIG. 4 is a cross-sectional view of an embodiment of an air bag to be preferably used with the present invention.

Needless to mention, the air bag 56 may be unitarily constructed so as to allow a uniform pressure throughout. Or, as shown in FIG. 4, the air bag 56 may be constructed with a large number of air chambers $56a_1$ through $56a_n$ and $56b_1$ through $56b_n$, and when the bed is used, the air pressure inside changes in order from air bag $56a_1$ located at the foot position to air bag $56a_n$ at the middle position and the same changes in order from air bag $56b_1$ at the head position to air bag $56b_n$ at the middle position. When a person lies on a bed constructed in such a manner, the blood in their body moves from the feet to the heart and from the head to the heart so that the circulation of the blood becomes smoother and thereby the person's health is promoted.

Furthermore, the light rays emitted from the optical conductor 52, as mentioned above, are radiated onto the human body lying on the bed. On that occasion, a part of the light rays emitted from the optical conductor 52 are discharged downward so that the discharged light rays cannot be used effectively. In order to prevent the light rays from being diffused, a reflecting plate 57 is disposed on the underside of the optical conductor 52 as shown in FIG. 4 (or FIG. 3). The light rays reflected on the reflecting plate 57 pass through the cloth 51. Consequently, the light rays emitted from the optical conductor 52 are effectively utilized.

The bed for light bathing, according to the present invention, is employed as mentioned above. On that occasion, the rear surface of the employed cloth covering is formed as a reflecting surface or an air bag is used as the cloth-covering, and furthermore the cloth on the internal side is constructed of a transparent substance.

Furthermore, in the case of constructing the external side cloth with a reflecting material, the light rays which pass through the cloth (bed sheet) 51 and dissipate without being radiated onto the human body can be reflected on the cloth covering and returned downward. Consequently, the light rays emitted from the optical conductor 52 can be utilized more and more effectively.

As is apparent from the foregoing description, the bed employed for light bathing according to the present invention has several advantages for a person who must keep lying on a bed as well as for a healthy person who can effectively take a light bath for the purpose of promoting health and receiving a beauty treatment.

I claim:

1. A bed employed for light bathing, comprising a bed frame having a first end and a second end along with a first side and a second side, a first elongated roller disposed along said first side of said bed frame and extending between said first and said second ends, a transparent cloth having a width greater than said bed frame, said cloth having a first end connected to said first roller, at least a first portion rolled around said first roller, a second stretched portion stretched across said bed frame, and a second end connected to said second roller, means for winding said second roller such that said second portion of said cloth is wound around said second roller as said first portion is unwound from said first roller and stretched across said bed frame, a plurality of elongated optical conductors on said bed frame and extending between said first and second ends of said bed frame, said optical conductors being arranged beneath the stretched portion of said transparent cloth for conducting one of the visible light rays component of solar rays and artificial light rays, said visible light rays component being devoid of ultraviolet and infrared rays and radiating the conducted visible light rays out of said optical conductors and through said transparent cloth, a reinforcing material stretched across said frame for preventing said transparent cloth from ripping and stretching, and a reflecting plate beneath said optical conductors for reflecting visible light rays radiated out of said optical conductors towards said transparent cloth.

2. A light-bathing bed as in claim 1, further comprising a transparent air bag stretched across said frame, said transparent air bag comprising a first plurality of chambers arranged sequentially from a position corresponding to a head position to a position corresponding to a mid-body position, and a second plurality of chambers arranged sequentially from a position corresponding to a foot position to a position corresponding to the mid-body position, the air pressure in each of said first plurality of chambers differing sequentially from said head position to said mid-body position, and the air pressure in each of said second plurality of chambers differing sequentially from said foot position to said mid-body position, whereby when a person lies on the bed, blood in the body circulates from the head to the heart and from the feet to the heart.

* * * * *